(12) United States Patent
Guracar

(10) Patent No.: US 6,544,184 B1
(45) Date of Patent: Apr. 8, 2003

(54) IMAGING WITH REDUCED ARTIFACTS FOR MEDICAL DIAGNOSTIC ULTRASOUND

(75) Inventor: Ismayil M. Guracar, Redwood City, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/942,009

(22) Filed: Aug. 28, 2001

(51) Int. Cl.$^7$ ................................................ A61B 8/14
(52) U.S. Cl. .................... 600/458; 600/437; 600/44; 600/447; 600/472
(58) Field of Search .................... 600/437, 441, 600/447, 458, 472

(56) References Cited

U.S. PATENT DOCUMENTS 5,456,257 A  * 10/1995 Johnson et al. ............. 600/453
5,709,210 A  *  1/1998 Green et al. ................ 600/453
6,117,082 A  *  9/2000 Bradley et al. ............. 600/458
6,131,458 A  * 10/2000 Langdon et al. ............ 600/443

* cited by examiner

Primary Examiner—Marvin M. Lateef
Assistant Examiner—William C. Jung

(57) ABSTRACT

Line synthesis avoids artifacts from differences in collateral destruction of contrast agent. Data representing a plurality of scan lines is received in response to each transmit event. Transmission and reception along the same scan lines are repeated a plurality of times for loss correlation imaging. Coherent data or data prior to detection along two or more scan lines is combined, removing differences. The combined data represents a synthesized line of data for detection. Line data representing contrast agents or not representing contrast agents may be synthesized from detected data. Detected data or data in the magnitude and phase domain representing two or more scan lines is combined. By altering the data provided to a flow processor or Doppler data detector, the relative phase of the data representing the two scan lines is determined. A magnitude for a synthetic line is calculated as a function of the magnitude of data representing two separate scan lines and the relative phase.

34 Claims, 3 Drawing Sheets

```
LINE #  1234567...
       eCCe
        eCCe
         eCCe
          eCCe
           eCCe
```

```
LINE #  1234567
       eCCe
       eCCe
       eCCe
        eCCe
        eCCe
        eCCe
         eCCe
         eCCe
         eCCe
          eCCe
          eCCe
          eCCe
```

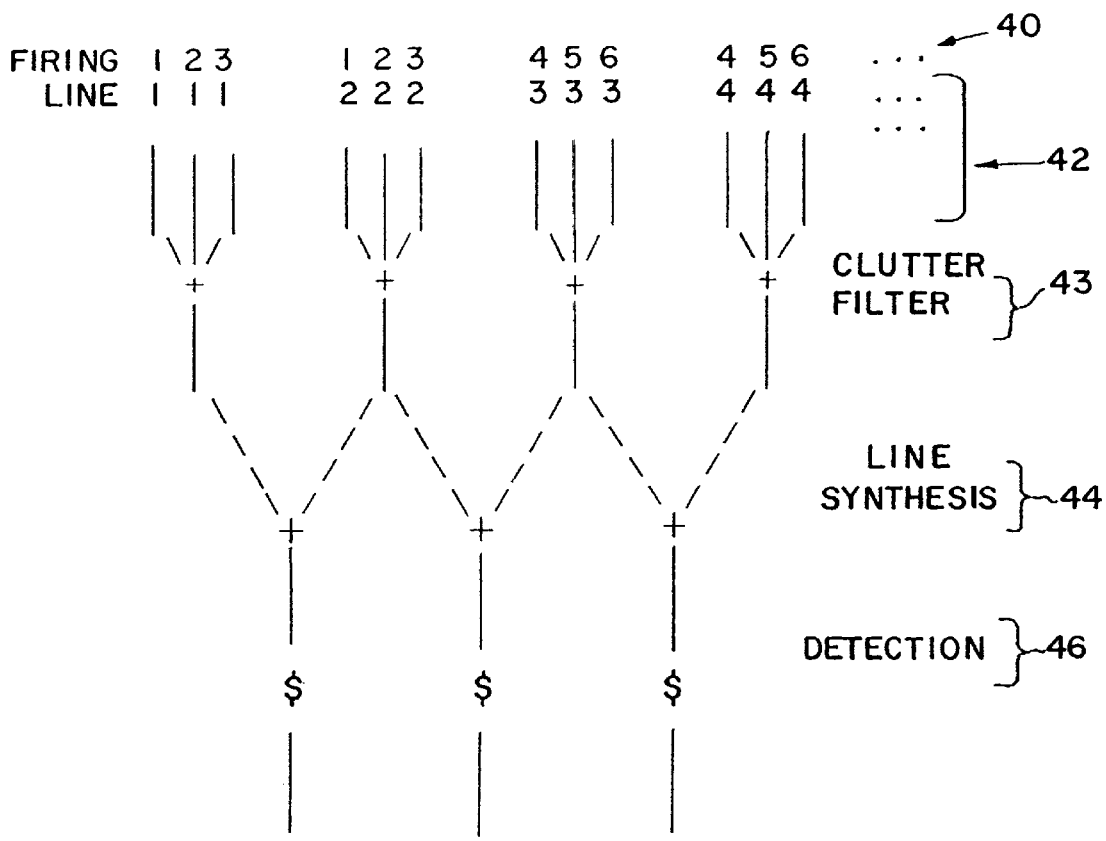

AUTOCORRELATION
CALCULATOR

IMAGING WITH REDUCED ARTIFACTS FOR MEDICAL DIAGNOSTIC ULTRASOUND

BACKGROUND

This invention relates to artifact reduction. In particular, scan line data is combined for reducing artifacts in contrast agent imaging.

Contrast agents, such as microspheres, are added into a patient to assist in medical diagnostic imaging. Contrast agents are sensitive to acoustic energies. Transmission of acoustic energy destroys or modifies the contrast agent. A loss of correlation due to changes of the contrast agent is determined and used to generate a medical diagnostic ultrasound image. In another method of detection, movement of the contrast agent without loss of correlation or in combination with some loss of correlation may be used to generate ultrasound images.

To determine the loss of correlation or movement of contrast agent, multiple beams of acoustic energy are transmitted along the same scan lines or to the same locations. Resulting echoes from the transmissions are sampled for determining the loss of correlation or movement.

Various transmit and associated energy sequences for a loss of correlation or motion detection imaging have been used. For example, a flow sample interleave ratio (FSIR) of 1 and a flow sample count (FSC) of 3 are used. As a result, three transmissions for three pulse repetition intervals are fired along each scan line before firing along another or adjacent line. For each scan line except the edge scan line for a region of an image, a pulse or energy sequence of eeeCCCeee is provided, where e represents energy from a transmit pulse along an adjacent scan line (i.e., e indicates energy at an edge of a transmit beam) and C represents energy from the transmit pulse centered along the transmit line of interest. Energy from transmit pulses along adjacent scan lines acts to destroy the contrast agent or cause collateral damage before transmissions for detecting movement or a loss of correlation sampling are fired. Where the collateral destruction or energy sequence is the same for each scan line, image artifacts may be avoided. However, where the energy sequence is different as a function of the scan line, image artifacts are created.

Receiving along multiple scan lines in response to a single transmit event may increase a frame rate. For example, in coherent contrast agent imaging, acoustic energy is received along two scan lines in response to a single transmit pulse or event. FIG. 1 represents a scanning sequence for a coherent contrast agent imaging process. In response to each transmit event, acoustic energy along two different scan lines is received. For each transmit event, the position of the transmitted energy and associated received focus is shifted. Acoustic energy along every scan line is subjected to the same collateral destruction and imaging destruction pattern: eCCe, avoiding contrast agent destruction artifacts. However, the process shown in FIG. 1 does not provide a level of sensitivity and agent specificity associated with the multiple pulse loss of correlation imaging methods described above.

BRIEF SUMMARY

The present invention is defined by the following claims, and nothing in this section should be taken as a limitation on those claims. By way of introduction, the preferred embodiments described below includes methods and systems for acquiring contrast agent data for imaging and for combining data representing different scan lines.

Line synthesis avoids artifacts from differences in collateral destruction of contrast agent. Data representing a plurality of scan lines is received in response to each transmit event. Transmission and reception along the same scan lines are repeated a plurality of times for loss correlation imaging. Coherent data or data prior to detection along two or more scan lines is combined, removing differences. The combined data represents a synthesized line of data for detection.

Line data representing contrast agents or not representing contrast agents may be synthesized from detected data. Detected data or data in the magnitude and phase domain representing two or more scan lines is combined. By altering the data provided to a flow processor or Doppler data detector, the relative phase of the data representing the two scan lines is determined. A magnitude for a synthetic line is calculated as a function of the magnitude of data representing two separate scan lines and the relative phase.

Further aspects and advantages of the invention are discussed below in conjunction with the preferred embodiments.

BRIEF DESCRIPTION OF SEVERAL VIEWS OF THE DRAWINGS

FIG. 4 is a graphical representation of one embodiment of a method for synthesizing line data.

FIG. 5 is a graphical representation of a pulse sequence showing centralized and edge energy of one embodiment.

DETAILED DESCRIPTION OF THE PREFERRED EMBODIMENTS

The preferred embodiments discussed below provide loss of correlation or motion imaging in response to multiple repetitions of receive events along a same scan line or scan lines with reduced artifacts. Synthesizing coherent data associated with two or more scan lines reduces artifacts in resulting images. By repeating transmission and reception along the same scan lines, the sensitivity and specificity to destruction or loss of correlation of ultrasound contrast agent is increased. The pulse sequences include reception along multiple scan lines in response to a single transmit event, increasing the frame rate without artifacts.

In one embodiment for imaging contrast agents or for imaging without contrast agents, a line of data is synthesized from detected data. By inserting low or null values into a stream of pre-detected data, the relative phase associated with the data for two different scan lines is determined from detected velocity estimates. The detected energy and velocity information is synthesized, and a combined magnitude value is calculated.

Figures 1, 2, 3:
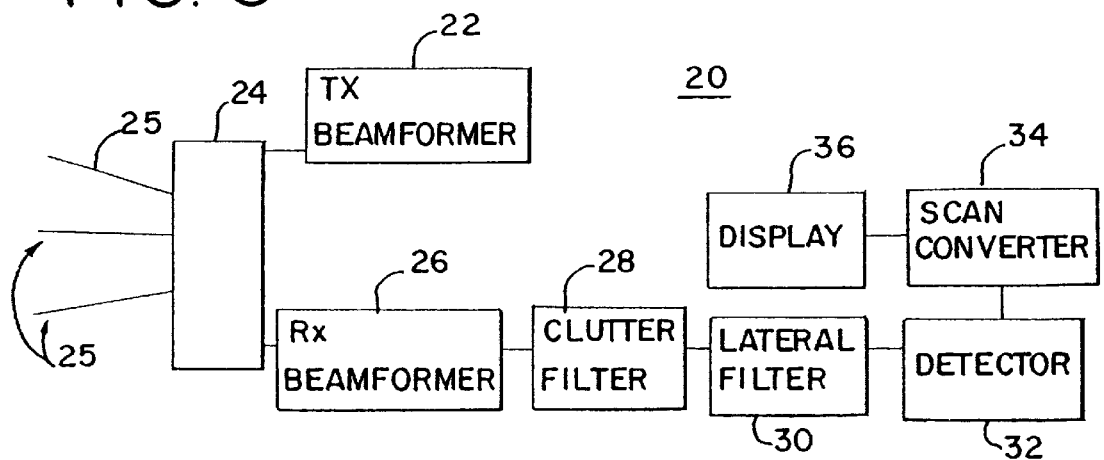
FIGS. 1 and 2 are graphical representations of two embodiments of pulse sequences showing center and edge energy.
FIG. 3 is a block diagram of one embodiment of an ultrasound system for line synthesis of coherent data.

FIG. 2 shows one embodiment of a pulse sequence for line synthesis. In this embodiment, echo signals are received along two scan lines in response to each transmit event, and three transmit events and associated receive events are provided for each pair of scan lines. After echo signals are received for scan lines 1 and 2, transmit and receive event sequences are repeated for scan lines 3 and 4. Each pair of scan lines is sampled three times at a given pulse repetition interval with the receive beamformer operating in a dual beam mode. While increasing the frame rate, a destruction artifact is generated. The even and odd numbered lines are exposed to different collateral damage. The even numbered lines are exposed to an acoustic energy sequence of CCCeee. The odd numbered lines are exposed to an acoustic energy sequence of eeeCCC. Less sensitivity to contrast agent destruction is provided on odd scan lines because of the collateral destruction (eee) before transmission and reception of signals associated with the scan line (CCC).

The difference in sensitivity may lead to a stripped pattern in a contrast agent image, particularly at low signal to noise ratios. Synthesizing complex predetected scan line data from a pair of even and odd scan lines removes the artifact with no or little loss of resolution. Each resulting synthesized line is a combination of the two different energy sequences.

FIG. 3 shows one embodiment of a medical diagnostic ultrasound system for synthesizing data from data representing two scan lines. The system 20 includes a transmit beamformer 22, a transducer 24, a receive beamformer 26, a clutter filter 28, a lateral filter 30, a detector 32, a scan converter 34, and a display 36. Additional, different, or fewer components may be used, such as combining the clutter filter 28 and lateral filter 30. In one embodiment, the ultrasound system 20 comprises a Sequoia®, Aspen™, or 128XP® ultrasound system manufactured by Acuson Corporation, but other ultrasound systems by other manufacturers or remote work stations may be used.

The transmit beamformer 22 comprises analog or digital circuitry for generating excitation waveforms in sequential transmit events. In one embodiment, the transmit beamformer 22 comprises a transmit beamformer disclosed in U.S. Pat. No. 5,675,554, the disclosure of which is incorporated herein by reference. Other transmit beamformers may be used, such as analog or memory based beamformers for generating unipolar, bipolar or sinusoidal modulated or unmodulated transmit waveforms. The transmit waveforms from the transmit beamformer 22 are provided to the transducer 24.

The transducer 24 comprises a linear, curvilinear, one-dimensional, two-dimensional, 1.5-dimensional, annular or other array of transducer elements. In one embodiment, the transducer 24 comprises piezoelectric materials, but electrostatic or capacitive membrane ultrasound transducers may be used. In response to the transmit waveforms, the transducer 24 transmits acoustic energy into a region of the patient. Based on delays and apodization applied to the transmit waveforms for the elements of the transducer 24, acoustic energy is focused along one or more scan lines 25. Transmit events may be repeated two or more times along the same scan line 25. Different delays and/or apodization is applied for transmitting along a different scan line. The region of the patient is scanned in any of various scan line formats, such as sector, linear, or Vector®. Where the region of the patient being scanned includes contrast agent, such as contrast agents perfused into tissue or in fluid regions, acoustic echo signals are responsive to the contrast agent. Acoustic echoes are received by the transducer 24 and converted to electrical signals.

A receive beamformer 26 comprises analog and/or digital circuitry for processing the electrical echo signals to represent the scan line or scanned region. In one embodiment, the receive beamformer 26 comprises a receive beamformer disclosed in U.S. Pat. No. 5,685,308, the disclosure of which is incorporated herein by reference. For motion detection and/or loss of correlation imaging of contrast agent, the receive beamformer 26 includes digital circuitry, buffers or memories sufficient to allow a flow sample interval rate of two or more with a flow sample count of two or more. For example, two banks of a 128 K byte memories are provided. Each bank of memory is operable to store data for 256 scan lines 25 with a total of 512 range samples. For a flow sample count of 3, each bank holds 85 receive lines. If the range grid is reduced to a maximum of 256 range samples, 170 scan lines may be received and stored. Samples are stored in groupings in the same banks of memory. The banks allow the processing of receive signals to keep pace with the acquisition. Other memory structures may be used, such as with more than two banks or dual port RAM.

The receive beamformer 26 applies various delays and apodization to electrical signals associated with the elements of the transducer 24 for receiving along multiple scan lines in response to a single transmit event. Different delays and/or apodization are applied to the same electrical signals to determine data representing two or more scan lines 25. The data is formatted as in-phase and quadrature data in one embodiment, but radio frequency data may be used.

The transmit beamformer 22 and receive beamformer 26 operate to maintain coherence between data received for different scan lines 25. The samples of two signals are coherent when sufficient information is stored, preserved or maintained to enable accurate characterization of the relative amplitude and phase of the complex envelopes of the two signals. Two echo or receive signals are referred to as phase-aligned if the only difference between their phase variations is due to the interaction of the signals with a target or targets. The process of phase-aligning two signals is a process of adjusting the temperal phase variations of one signal or the other or both for systematic distorting influences. By phase-aligning the coherent data, the receive beamformer 26 allows subsequent synthesization of data from two different scan lines without introducing error due to phase differences. In one embodiment, the receive beamformer 26 operates as described in U.S. Pat. No. 5,623,928 (Method And Apparatus For Coherent Image Formation), the disclosure of which is incorporated herein by reference. The receive beamformer 26 phase corrects the data representing one or more of the scan lines for subsequent line-to-line analytic processing (i.e., combining or synthesizing). For example, the receive beamformer 26 includes a complex multiplier and associated control devices for adjusting the phase of complex data. In alternative embodiments, phase correction for synthesis is performed by the clutter filter 28 or the lateral filter 30.

The clutter filter 28 comprises a digital signal processor, application specific integrated circuit (ASIC), analog components, digital components or other devices for high-pass or low-pass filtering to remove signals associated with tissue or flow. In one embodiment, the clutter filter 28 comprises a clutter filter provided with Doppler or flow processors or detectors. The clutter filter 28 receives samples, such as in-phase and quadrature data, associated with the same scan line 25 for filtering. The cutoff frequency is selected to remove signals associated with moving tissue or low flow and pass signals associated with loss of correlation or vice versa.

The lateral filter 30 comprises a digital signal processor, ASIC, analog circuitry, digital circuitry or other devices for filtering between scan lines 25. For example, a fmite impulse response filter is used. The lateral filter 30 azimuthally filters to combine or synthesize phase-aligned data from different scan lines. In one embodiment, the lateral filter 30 includes circuitry or processes for phase-aligning data associated with different scan lines 25. For example, two sets of data associated with two scan lines 25, respectively, are combined in response to a two tap lateral filter. In one embodiment, equal coefficients, such as [1 1], are used in the lateral filter 30 for combining, but unequal coefficients may be used. In other embodiments, three or more taps are provided. The lateral filter 30 and clutter filter 28 may be combined, resulting in one filtering operation for performing both clutter and synthesis filtering.

The detector 32 comprises one or more general processors, FPGA, digital signal processor, ASICs, analog circuits, digital circuits or other devices. In one embodiment, the detector 32 comprises a Doppler or color flow processor, but a B-mode processor may alternatively or additionally be included. The detector 32 detects contrast agent information from the synthesized scan line data. For example, the loss of correlation between two or more samples from a same location of a patient is detected. The detector 32 determines a difference in energy or velocity between samples representing the same location at different times. As another example, the detector 32 comprises a B-mode detector. The amplitude, intensity, energy, or power of the envelope signal is detected. The detected information is log compressed. Other detection techniques and associated circuitry may be used.

Other processing may be performed by the detector 32. For example, conventional color flow processing may be used. Energy, variance and/or velocity signals may be detected and displayed. Other techniques may be used, such as pulse inversion (see U.S. Pat. Nos. 5,951,478, and 5,632,277) or a pulse inversion Doppler (see U.S. Pat. No. 6,095,980). Contrast pulse sequences or detecting odd and even order scattering (see U.S. application Ser. No. 09/514,803) may also be used. All of the aforementioned techniques vary the amplitude and/or phase on transmit and/or receive between pulses within a flow sample count to improve contrast agent imaging. Any differences in phase is accounted for in the phase correction for synthesizing data.

The detector 32 may include additional filtering circuitry. For example a spatial filter filters samples of detected intensities associated with different locations within a scan region. Spatial filter coefficients are selected such that reduced sensitivity to variations in energy sequences across scan lines 25 is provided. For example, a spatial filter that varies coefficients as a function of scan line is provided.

The scan converter 34 comprises circuitry for converting data from a polar coordinate scan format into a Cartesian coordinate format for display. The display 36 comprises a monitor or other device for providing an ultrasound image responsive to the received echo signal. In one embodiment, the image comprises a loss of correlation or motion detection image of a region including contrast agents. For example, a loss of correlation image associated with synthesized line data is generated as an overlay image section of a larger B-mode image. Other combinations of images and associated overlays including loss of correlation, Doppler, and B-mode imaging may be used.

FIG. 4 illustrates detecting contrast agent using reception along multiple scan lines 25 for each receive event and line synthesis to reduce or remove artifacts. Acoustic energy is transmitted in two or more transmit events at 40. Six transmit events are shown in detail, but additional transmit events are provided. As illustrated, the flow sample count is 3, such that 3 transmit and subsequent receive events are associated with the same scan lines 25. Other flow sample counts may be used such as one, two, four or more. In the first receive event, data is received and acquired along first and second scan lines. The data samples represent those scan lines as shown at 42. Data representing the first and second scan lines is acquired in response to second and third receive events in response to sequential transmit events. The transmit and reception sequence shown at 42 is similar or the same as the transmit and receive sequence discussed above for FIG. 2. After the flow sample count is complete, the transmit and receive sequence continuous for scan lines 3 and 4 or other scan lines. Samples representing two scan lines 25 are acquired in response to each transmit event. As discussed above, with respect to FIG. 2, data representing each of the scan lines 25 is subjected to different amounts of collateral destruction of contrast agent from transmissions along adjacent scan lines.

At 43, data representing the same scan lines 25 and associated with multiple receive events is clutter filtered. For example, three sets of data associated with three receive events along one scan line are clutter filtered. In one embodiment, the clutter filter comprises a three-tap filter using coefficients [1−2 1]. Other coefficients with greater or lesser number of input data may be used. The clutter filter receives pre-detected data, such as in-phase and quadrature data, and outputs a set of coherent pre-detected line samples representing the received signals along the scan line 25.

Prior to detection, data representing different scan lines 25 is combined as shown at 44. Coherent data, such as in-phase and quadrature data, output by the clutter filter 28 or receive beamformer 26 is combined. The data represents different scan lines 25 and associated different collateral destruction of contrast agents. For each range, two samples are combined. For example, each sample comprises in-phase and quadrature data (I1+jQ1, I2+jQ2). The in-phase and quadrature information is combined, providing a sample corresponding to I1+I2+j (Q1+Q2). The two sets of data are combined to form a synthesized line of data. Prior to combination, the two sets of data representing two different scan lines 25 are phase-aligned. For example the receive beamformer 26 phase aligns the data or a complex multiplier for phase aligning the data is included in the lateral filter 30.

The data is combined by the lateral filter 30. In one embodiment, the filter applies substantially equal coefficients, such as [1 1] to the two sets of data for combination. In other embodiments, three or more taps are provided for the lateral filter 30 or unequal coefficients are used. As shown in FIG. 4, a synthesized line is provided for each adjacent pair of scan lines, such as providing a synthesized line of data for a combination of scan lines 1 and 2, 2 and 3, 3 and 4, and so on.

At 46, the synthesized lines of data are detected by the detector 32. For example, a loss of correlation is determined using a Doppler detector or intensities are determined using a B-mode detector. Synthesized and detected data are used to generate an image or an overlay image section. For example, a B-mode image is generated with or without line synthesis processing. An overlay image section for the B-mode image is generated in response to synthesized data. Other combinations of images may be used.

In other alternative embodiments, data for three or more scan lines is received in each or one receive event. FIG. 5 shows receiving data along three scan lines with a flow sample count of 3. Different collateral destruction is provided for each of the scan lines. For example, scan line 4 is responsive to an acoustic energy sequence of eeeCCC, middle scan line 5 is responsive to the acoustic energy sequence of CCC and the scan line 6 is responsive to acoustic energy sequence of CCCeee. For this embodiment, the lateral filter 30 synthesizes three lines of data corresponding to the three different types of collateral destruction or the three receive beams. The three sets of data are combined in response to a three-tap filter with equal or substantially equal coefficients.

Figure 6:
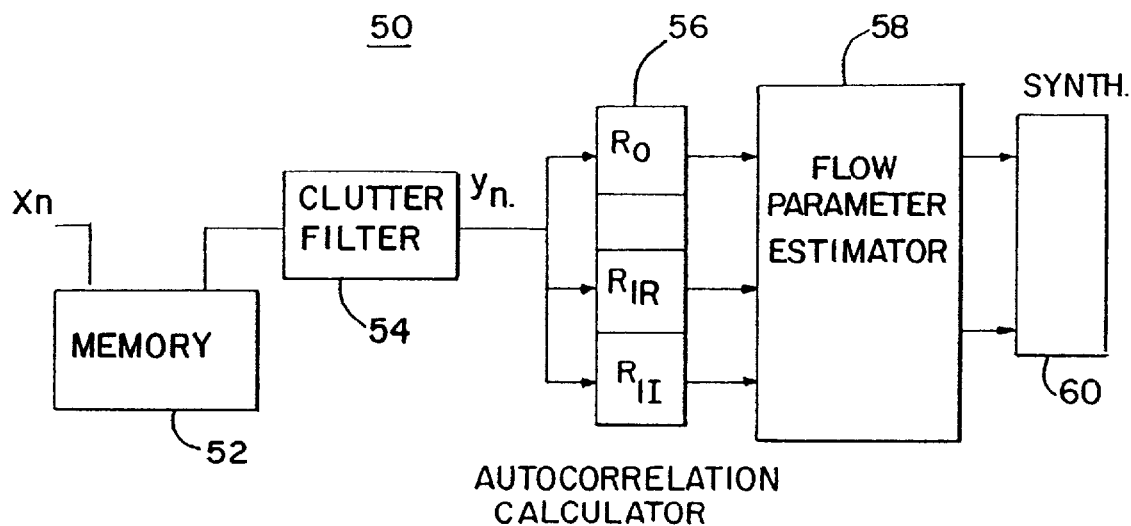
FIG. 6 is a block diagram of one embodiment of an ultrasound system for synthesizing line data in the magnitude domain.

In alternative embodiments, line synthesis is performed after detection. scan line data is combined in the magnitude and phase domain. FIG. 6 shows a system 50 for synthesizing data representing different scan lines 25 after detection. In one embodiment, the system 50 replaces the clutter filter 28, lateral filter 30 and detector 32 of FIG. 3. The system 50 includes a memory 52, a clutter filter 54, autocorrelation calculator 56, a flow parameter estimator 58, and a synthesizer 60. Additional, fewer, or different components may be used. The memory 52 comprises a corner turning memory, RAM or other data storage device for storing coherent data from the receive beamformer 26. The memory 52 is operable to insert no or low-value data within a string or sequence of data.

The clutter filter 54 comprises any the clutter filters discussed above. The strings of data representing the same scan lines with any inserted data are clutter filtered.

The autocorrelation calculator 56 comprises a digital signal processor, FPGA, ASIC or other device such as a flow or Doppler processor. The flow parameter estimator 58 also comprises an additional signal processor, ASIC or other device. In one embodiment, the autocorrelation calculator 56 and the flow parameter estimator 58 comprise a Doppler or flow processor for detecting energy and velocity information from data output by the clutter filter 54.

The synthetic line device 60 comprises a digital signal processor, FPGA, ASIC or other device for phase-align and combining data representing two different scan lines. In one embodiment, the synthetic line device 60 is incorporated within the Doppler or flow processor. In alternative embodiments, the synthetic line device 60 comprises a lookup table to determine a magnitude of a synthesized line sample as a function of detected energies and phases associated with two different scan lines. The synthetic line device 60 is operable to determine the phase relationship or differences in velocities output by the flow parameter estimator 58 and synthesize a magnitude as a function of energies output by the flow parameter estimator 58 and the difference in velocity or relative phase.

Figure 7:
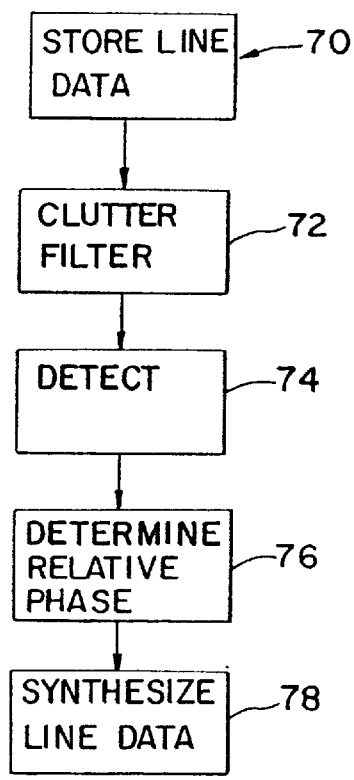
FIG. 7 is a flow chart of one embodiment of a method of the synthesis of line data in the magnitude domain.

FIG. 7 shows a flow chart of one embodiment for synthesizing or combining line data from detected data. Representation of samples as a magnitude and phase is more compact than as coherent in-phase and quadrature data, allowing for more efficient processing. Converting between rectangular to polar or polar to rectangular may require expensive componentry. By providing line synthesis of detected data, conversion to a polar coordinate is performed once and subsequent processing remains within the polar domain.

In Act 70, scan line data is stored. Data representing one or more, such as two scan lines 25 is stored. One set or multiple sets of data representing the same scan line is stored. In one embodiment, the scan line data comprises in-phase and quadrature coherent data. The data is responsive to sequential transmit and receive events or multiple lines of data responsive to a single transmit and receive event, such as associated with single or multiple scan line reception during a receive event, respectively. The scan line data is responsive to contrast agents in one embodiment. In alternative embodiments, the scan line data is responsive to tissue or fluids free from contrast agent.

For line synthesis, each of the strings of scan line data output from the memory is altered. In one embodiment, small or null values are inserted within a string of data. For example, three samples representing the same scan line at a same depth are provided, $X_0$, $X_1$, and $X_2$. Out of a possible 1,024 magnitude values (e.g., values −512 through 511), a 1 or 0 value is inserted between each of the samples output for clutter filtering. For example, the string is altered to comprise $X_0$, 1, $X_1$, 0, $X_2$, 0. Insertion of the null or low-values allows for velocity estimates to reflect phase, maintaining coherency of the data after detection.

The strings of data representing the same scan line with inserted values are output to the clutter filter in act 72. The clutter filter applies coefficients that include null-values for maintaining the phase relationship after detection. Other coefficient values used comprise coefficient values typically used for clutter filtering, such as the [1−2 1] clutter filter coefficients discussed above. Given the low or null values, the clutter filter applies the coefficients as a set of $C_0$, 0, $C_1$, 0, $C_2$. As a result, the clutter filter outputs a sequence of $Y_0=2C_0X_0+C_1X_1+C_2X_2$ and $Y_1=C_0$. $Y_0$ and $Y_1$ values are output by the clutter filter for each range sample along a scan line. The clutter filter 54 outputs samples associated with two or more scan lines to the autocorrelation calculator 56.

The energy and velocity are detected in act 74. Line data representing a single scan line 25 is autocorrelated to determine energy and velocity. In response to the in-phase and quadrature data with the inserted null and low-values, a first order and real and imaginary second order autocorrelation coefficients are calculated. The first order of autocorrelation coefficient, $R_0=Y_0^2+Y_1^2$. The second order autocorrelation coefficient is equal to $Y_0 Y_1$. If clutter coefficient $C_0$ is small relative to the multiple of a clutter coefficient and one of the input sequence values, $C_N X_N$, the first order autocorrelation coefficient is equal to: $|C_0X_0+C_1X_1+C_2X_2|^2$. The second order autocorrelation coefficient is equal to $(C_0X_0+C_1X_1+C_2X_2)C_0$. The autocorrelation coefficients are calculated for each scan line to be synthesized or combined. For example, autocorrelation coefficients are calculated for pairs of scan lines.

The flow parameter estimator 58 estimates the energy and velocity from the autocorrelation coefficients. The energy, ENE, is equal to $20 \log_{10}\sqrt{I^2+Q^2}$. The phase from each sample is given as $P_1$=angle (I+jQ). To determine an original amplitude of a signal from the energy, the following formula is used: $A_1=\sqrt{10^{(E_1/10)}}$. $I_1=A_1 \cos (P_1)$ and $Q_1=A_1 \sin (P_1)$. The energy is equal to $10 \log_{10}(R_0)$ or ENE=$10 \log_{10} |C_0X_0+C_1X_1+C2X_2|^2$. The velocity is equal to the angle of the second order autocorrelation coefficient, VEL=angle $(C_0X_0+C_1X_1+C_2X_2)$, if a first clutter filter coefficient is a real value. In response to the insertion of the small or null values into the string of data representing a scan line, the velocity represents the phase.

Using coherent data before detection, a synthesized line sample from samples of two different scan lines is represented at $Y_S=I_1+I_2+j(Q_1+Q_2)$. The magnitude of the synthesized line is derived as $A_S^2=|Y_S|^2$. Substituting for the amplitude and phase equation discussed above, $A_S^2=A_1^2+A_2^2+2A_1A_2 \cos(P_1-P_2)$, where $A_1$ and $P_1$ correspond to the detected amplitude and phase of a first scan line and $A_2$ and $P_2$ correspond to the amplitude and phase of a second scan line. The energy of the synthesized line is equal $10 \log_{10} (A_S^2)=10 \log_{10} (A_1^2=A_2^2+2A_1A_2 \cos (P_1-P_2))$.

In act 76 the relative phase is determined. The phase relationship is calculated as a function of the velocities output by the flow parameter estimator 58. Since the velocities represent the phase, the difference in velocity representing two different scan lines is calculated. Other functions for determining the relative phase may be used, including functions accounting for various phase adjustments for transmission and reception for imaging.

In act 78, the synthesized line data is determined as a function of the phase relationship. The magnitude of the synthetic line sample is determined as an energy value discussed above. The amplitude values $A_1$ and $A_2$ are calculated from the energy values output by the flow parameter estimator 58 using an antilog function. The magnitude or energy, Es, is calculated as discussed above as a function of the relative phase or phase difference and energies. In one embodiment, a lookup table is provided. The energy values for two scan lines and the cosine of the phase difference or difference in velocities for the two scan lines are input into the lookup table. The magnitude is output from the lookup table. In alternative embodiments, a processor or ASIC calculates the magnitude or energy of the synthetic line. Piecewise linear approximations may be used to simplify and speed up calculations without requiring conversion to coherent in-phase and quadrature data.

Synthesizing line data using detected magnitude and phase information may be used where data representing a single scan line is received during each transmit event. In yet other alternative embodiments, data representing three or more scan lines is combined or synthesized to reduce artifacts. Synthesizing data associated with two scan lines in the magnitude and phase domain may also be used for analytic line interpolation, such as described in U.S. Pat. No. 5,623,928. For example, an analytic line is interpolated between two scan lines. Data for each of the scan lines and the analytic line are separately used for generating an image. Interpolation of data on the range dimension or other range filtering operations may also be synthesized using magnitude and phase domain or detected data. Phase correction for any use may be performed by adjusting a detected phase or as a function of line-to-line phase differences in the magnitude and phase domain rather than using a complex multiplier on complex in-phase and quadrature data.

While the invention has been described above by reference to various embodiments, it would be understood that many changes and modifications can be made without departing from the scope of the invention. For example, synthesizing line data has a function of phase differences with detected data is used in association with reception of a single scan line during receive events responsive or not responsive to contrast agents. As another example, receiving data for two or more scan lines during a single receive event can be combined or synthesized prior to or after detection. As yet another example, line synthesis using any of the methods discussed herein can be used for B-mode imaging.

It is therefore intended that the foregoing detailed description be understood as an illustration of the presently preferred embodiments of the invention, and not as a definition of the invention. It is only the following claims, including all equivalents, which are intended to define the scope of the invention.

What is claimed is:

1. A method for acquiring contrast agent data for imaging with an ultrasound system, said method comprising the acts of:
   (a) acquiring first and second ultrasound data representing first and second scan lines, respectively, said first and second ultrasound data corresponding to different collateral destruction of contrast agent, said first and second scan lines spaced from an edge line; and
   (b) combining said first and second ultrasound data prior to detection.

2. The method of claim 1 wherein (a) comprises acquiring each of said first and second ultrasound data both in response to sequential first and second transmit events.

3. The method of claim 2 further comprising:
   (c) clutter filtering data corresponding to said first scan line and said first and second transmit events; and
   (d) clutter filtering data corresponding to said second scan line and said first and second transmit events.

4. The method of claim 1 wherein (a) comprises acquiring said first and second ultrasound data in response to first and second transmit events, respectively.

5. The method of claim 1 wherein (b) comprises filtering said first and second ultrasound data in response to substantially equal filter coefficients.

6. The method of claim 1 further comprising:
   (c) detecting the combined data of (b).

7. The method of claim 1 further comprising:
   (c) generating a B-mode image; and
   (d) generating an overlay image section with the B-mode image, said overlay image section responsive to the combined ultrasound data of (b).

8. The method of claim 1 wherein (b) comprises combining ultrasound data corresponding to at least three scan lines.

9. The method of claim 1 wherein (a) comprises acquiring the first, the second, and third ultrasound data in response to sequential first, second, third transmit events.

10. An ultrasound system for acquiring ultrasound data representing contrast agents in a patient, said ultrasound system comprising:
    a receive beamformer operative to acquire first and second ultrasound data representing first and second scan lines, respectively, said first and second ultrasound data corresponding to different collateral destruction of contrast agent, said first and second scan lines spaced from an edge line; and
    a filter for combining said first and second ultrasound data prior to detection.

11. The ultrasound system of claim 10 further comprising:
    a clutter filter for generating said first ultrasound data from scan line data corresponding said first scan line and first and second transmit events for generating said second ultrasound data from scan line data corresponding to the second scan line and said first and second transmit events.

12. The ultrasound system of claim 10 wherein said filter comprises a filter responsive to substantially equal filter coefficients.

13. The ultrasound system of claim 10 further comprising:
    a detector responsive to the output of said filter.

14. A method for imaging contrast agents with an ultrasound system, said method comprising the acts of:
    (a) receiving first and second ultrasound signals representing first and second scan lines, respectively, within a patient with contrast agent in response to a first transmission;
    (b) receiving third and fourth ultrasound signals representing the first and second scan lines, respectively, in response to a second transmission;
    (c) forming a second line ultrasound signal as a function of the first and third ultrasound signals;

(d) forming a second line ultrasound signal as a function of the second and fourth ultrasound signals;

(e) combining said first and second line ultrasound signals;

(f) detecting ultrasound data as a function of a result of (e).

15. The method of claim 14 wherein (c) and (d) comprise clutter filtering.

16. The method of claim 14 wherein (e) comprises filtering in response to substantially equal coefficients.

17. The method of claim 14 wherein (e) comprises synthesizing coherent data.

18. The method of claim 14 further comprising:

(g) generating a B-mode image; and (h) generating an overlay image section with said B-mode image, said overlay image section responsive to the detected ultrasound data of (f).

19. A method for combining ultrasound data representing different scan lines, said method comprising the acts of:

(a) detecting first and second ultrasound data representing first and second scan lines, respectively;

(b) determining a relative phase of the first ultrasound data to the second ultrasound data; and (c) determining a magnitude as a fiction of said relative phase and said first and second ultrasound data.

20. The method of claim 19 wherein (a) comprises detecting first and second energy values.

21. The method of claim 19 further comprising:

(d) inserting small or null values in a string of in-phase and quadrature data; and (e) clutter filtering said small or null values and said string of in-phase and quadrature data;

wherein the clutter filtered ultrasound data is detected.

22. The method of claim 19 wherein (b) comprises:

(b1) detecting first and second velocities as a function of in-phase and quadrature data and small or null values; and (b2) determining a difference between the first and second velocities.

23. The method of claim 19 wherein (e) comprises determining said magnitude as a function of a cosine of the phase difference.

24. The method of claim 19 further comprising:

(d) receiving line data responsive to contrast agent at said first and second scan lines; wherein said first and second ultrasound data is detected from line data.

25. The method of claim 24 wherein (d) comprises receiving said line data for both the first and second scan lines in response to both of sequential transmit events.

26. An ultrasound system for combining ultrasound data representing different scan lines, said ultrasound system comprising:

a flow processor operative to detect first and second ultrasound data representing first and second scan lines, respectively; and a synthetic line device operative to determine a relative phase of the first ultrasound data to the second ultrasound data and determine a magnitude as a function of said relative phase and said first and second ultrasound data.

27. The system of claim 26 wherein the flow processor is operative to detect first and second energy values.

28. The system of claim 26 further comprising: a clutter filter operative to filter small or null values in a string of in-phase and quadrature data, the output of said clutter filter connected with said flow processor.

29. The system of claim 26 wherein said flow processor is operative to detect first and second velocities as a function of in-phase and quadrature data and small or null values; and wherein said synthetic line device is operative to determine a difference between the first and second velocities.

30. A method for combining ultrasound data representing different scan lines, said method comprising the acts of:

(a) calculating a phase relationship between first and second ultrasound data; and (b) synthesizing line data from detected ultrasound data as a function of said phase relationship.

31. The method of claim 30 wherein (a) comprises:

(a1) detecting first and second velocities from said first and second ultrasound data; and (a2) calculating a difference between said first and second velocities.

32. The method of claim 31 wherein (a1) comprises detecting said first and second velocities from said first and second ultrasound data comprising in-phase and quadrature data and from small or null data.

33. The method of claim 30 wherein (b) comprises determining a magnitude as a function of said phase relationship and said first and second ultrasound data.

34. The method of claim 30 wherein the detected data is responsive to contrast agent.

* * * * *